(12) United States Patent
Walker et al.

(10) Patent No.: US 6,342,498 B1
(45) Date of Patent: Jan. 29, 2002

(54) ARYLPIPERAZINES AS SEROTONIN REUPTAKE INHIBITORS AND 5-HT$_{1D\alpha}$ ANTAGONISTS

(75) Inventors: Clint Duane Walker; David Taiwai Wong, both of Indianapolis; Yao-Chang Xu, Fishers, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/509,957

(22) PCT Filed: Oct. 21, 1998

(86) PCT No.: PCT/US98/22265
§ 371 Date: Mar. 31, 2000
§ 102(e) Date: Mar. 31, 2000

(87) PCT Pub. No.: WO99/20621
PCT Pub. Date: Apr. 29, 1999

Related U.S. Application Data

(60) Provisional application No. 60/063,493, filed on Oct. 22, 1997.

(51) Int. Cl.$^7$ .................. A61K 31/496; C07D 401/06; C07D 401/12
(52) U.S. Cl. .................. 514/253.09; 544/364
(58) Field of Search ............... 544/364; 514/253.09

(56) References Cited

U.S. PATENT DOCUMENTS 4,148,895 A   4/1979   Lattrell et al. ......... 424/248.54

FOREIGN PATENT DOCUMENTS

WO    WO 96/26936    9/1996

OTHER PUBLICATIONS

Saxena, Pramod R., Serotonin Receptors: Subtypes, Function Responses and Therapeutic Relevance. *Pharmacology and Therapeutics*, May 1995, 66:339–368.

*Primary Examiner*—Emily Bernhardt
(74) *Attorney, Agent, or Firm*—Charles T. Joyner; Nelsen L. Lentz

(57) ABSTRACT

Anylpiperazines of formula (1) useful as serotonin reuptake inhibitors and 5-HT1Dα receptor antagonists are disclosed herein:

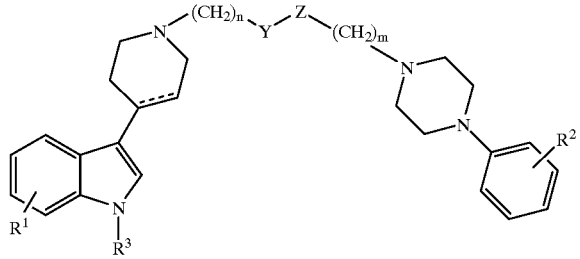

wherein
- $R^1$ and $R^2$ are each independently hydrogen, halo, —($C_1$–$C_6$)alkyl or —($C_1$–$C_6$)alkoxy;
- $R^3$ is hydrogen or —($C_1$–$C_6$)alkyl;
- Y is —CO— or —$CH_2$—;
- Z is —NH—, —N(COR)— or —$CH_2$— where R is —($C_1$–$C_6$)alkyl or —($C_3$–$C_8$)cycloalkyl;
- ═══ represents a double or single bond;
- n and m are an each independently integer from 1 to 3, both inclusive; or a pharmaceutically acceptable salt thereof.

9 Claims, No Drawings

ARYLPIPERAZINES AS SEROTONIN REUPTAKE INHIBITORS AND 5-HT$_{1D\alpha}$ ANTAGONISTS This is a 371 of PCT/US98/22265 filed Oct. 21, 1998 which claims priority to U.S. Provisional Application No. 60/063,493, filed Oct. 22, 1997.

The present invention belongs to the fields of pharmacology and medicinal chemistry, and provides new pharmaceuticals which are useful for the treatment of diseases which are caused or affected by disorders of the serotonin-affected neurological systems, particularly those relating to increasing the level of serotonin in the brain and inhibiting the serotonin $1_{D\alpha}$ receptor.

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generation of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistamine or anti-alpha-adrenergic activity. More recently, it has become possible to study the function of drugs at individual receptors in vitro or ex vivo, and it has also been realized that therapeutic agents free of extraneous mechanisms of action are advantageous to the patient. Accordingly, the objective of research now is to discover agents which affect only functions of serotonin, for example, at specific identifiable receptors.

Perhaps the most dramatic discovery in medicinal chemistry in the recent past is fluoxetine, a serotonin reuptake inhibitor, which is extremely effective in the treatment of depression. As a reuptake inhibitor, it increases the availability of serotonin in the synapse by reducing the uptake of serotonin by the serotonin uptake carrier. Dysfunction of the serotonin neurons resulting from excessive uptake results in depression, as well as other pathologies of the central nervous system. Not only is fluoxetine spectacularly effective in depression, it is also effective in treating numerous other conditions.

Over the last several years it has become apparent that serotonin is associated directly or indirectly with a number of physiological phenomena, including appetite, memory, thermo-regulation, sleep, sexual behavior, anxiety, depression, and hallucinogenic behavior [Glennon, R. A., J. Med. Chem., 30, 1 (1987)].

5-HT receptors have been identified in the central nervous system (CNS; brain and spinal cord) and in peripheral tissues including the gastrointestinal tract, lung, heart, blood vessels, and various other smooth muscle tissues.

It has been recognized that there are multiple types of 5-HT receptors. These receptors have been classified as 5-HT$_1$, 5-HT$_2$ and 5-HT$_3$ receptors, with the former being further divided into the sub-classes 5-HT$_{1A}$, 5-HT$_{1B}$, 5-HT$_{1C}$, 5-HT$_{1D}$, 5-HT$_{1E}$ and 5-HT$_{1F}$.

Few ligands have selectivity for 5-HT$_{1D}$ receptors. Sumatriptan possesses limited 5-HT$_{1D}$ selectivity. GR 127935 has also been identified as a potent and selective 5-HT$_{1D}$ receptor antagonist. Hayer, et al., *Pharmacological Reviews*, Vol. 46, No. 2, pp. 157–203 (1994).

Molecular cloning has demonstrated that pharmacologically defined 5-HT$_{1D}$ receptors are encoded by two separate but closely related genes, designated 5-HT$_{1D\alpha}$ and 5-HT$_{1D\beta}$, which are members of the GPRC superfamily. These receptors display highly conserved transmembrane homology (75%) and similar binding properties and second messenger coupling (inhibition of adenylate cyclase). Leonhardt, S., et al., *J. Neurochem*, 53:465–471 (1989).

It is desirable to develop new compounds and treatments for 5-HT$_{1D\alpha}$ receptor mediated diseases and diseases mediated by inhibiting the reuptake of serotonin.

We have now discovered a class of compounds which have activity at the 5-HT$_{1D\alpha}$ receptor and which inhibit the reuptake of serotonin.

This invention provides a compound of formula I

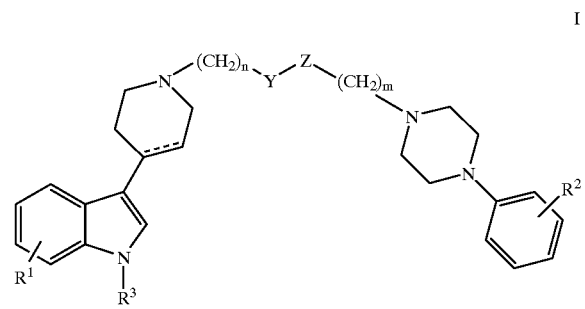

I wherein

R$^1$ and R$^2$ are each independently hydrogen, halo, —(C$_1$–C$_6$)alkyl or —(C$_1$–C$_6$)alkoxy;

R$^3$ is hydrogen or —(C$_1$–C$_6$)alkyl;

Y is —CO— or —CH$_2$—;

Z is —NH—, —N(COR)— or —CH$_2$—, where R is —(C$_1$–C$_6$)alkyl or —(C$_3$–C$_8$)cycloalkyl;

=== represents a double or single bond; and n and m are each independently an integer from 1 to 3, both inclusive; or a pharmaceutically acceptable salt or solvate thereof.

This invention also provides a pharmaceutical formulation comprising a compound of formula I in association with one or more pharmaceutically acceptable diluents, carriers and excipients.

This invention further provides a method of inhibiting the reuptake of serotonin comprising administering to a mammal in need thereof, a therapeutically effective amount of a serotonin reuptake inhibitor of formula I.

This invention provides in addition a method of inhibiting the 5-HT$_{1D\alpha}$ receptor comprising administering to a mammal in need thereof a therapeutically effective amount of a direct acting 5-HT$_{1D\alpha}$ antagonist of formula I.

This invention further provides a method of inhibiting the reuptake of serotonin and inhibiting the 5-HT$_{1D\alpha}$ receptor comprising administering to a mammal in need thereof a therapeutically effective amount of a serotonin reuptake inhibitor and 5-HT$_{1D}$ antagonist of formula I.

This invention also provides a method of alleviating the pathological effects of diseases mediated by inhibiting the reuptake of serotonin which comprises administering to a mammal in need thereof a therapeutically effective amount of a serotonin reuptake inhibitor of formula I.

Still further, this invention also provides a method of alleviating the pathological effects of diseases mediated by inhibiting the 5-HT$_{1D\alpha}$ receptor which comprises administering to a mammal in need thereof a therapeutically effective amount of a direct acting 5-HT$_{1D\alpha}$ antagonist of formula I.

This invention also provides a method of alleviating the pathological effects of diseases mediated by inhibiting the reuptake of serotonin and inhibiting the 5-HT$_{1D\alpha}$ receptor which comprises administering to a mammal in need of such treatment a therapeutically effective amount of a serotonin reuptake inhibitor and 5-HT$_{1D\alpha}$ antagonist of formula I.

Another aspect of the invention is a method of treating a mammal suffering from or susceptible to depression or anxiety; which comprises administering to a subject in need of such treatment a therapeutically effective amount of a compound of Formula I.

Yet another aspect of the invention is a method of treating a condition chosen from the group consisting of obsessive-compulsive disease, obesity, migraine, pain, particularly neuropathic pain, bulimia, premenstrual syndrome or late luteal syndrome, alcoholism, tobacco abuse, panic disorder, anxiety, post-traumatic syndrome, memory loss, dementia of aging, social phobia, attention-deficit hyperactivity disorder, disruptive behavior disorders, impulsive control disorders, borderline personality disorder, chronic fatigue syndrome, premature ejaculation, erectile difficulty, anorexia nervosa, disorders of sleep, autism, mutism and trichotilomania, which comprises administering to a subject in need of such treatment a therapeutically effective amount of a compound of Formula I.

A still further aspect of the invention is a method of treating a mammal suffering from or susceptible to dementia, Parkinson's disease, anxiety, appetite modulation, sexual dysfunction, seasonal affective disorder, hyperprolactinemia, cerebral vascular disease, antisocial behavior, obsessive/compulsive disorder, amnesia, tardive dyskensia, hypertension and gastric motility disorder, which comprises administering to a subject in need of such treatment, a therapeutically effective amount of a compound of formula I.

Other objects, features and advantages of the present invention will become apparent from the subsequent description and the appended claims.

Definitions:

As used herein, the term, "$(C_1–C_6)$alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, isopentyl, neopentyl, heptyl, hexyl and the like.

The term "$(C_1–C_{10})$alkyl" encompasses "$(C_1–C_4)$alkyl".

The term "halo" means fluoro, chloro, bromo or iodo.

The term "$(C_1–C_6)$alkoxyl", as used herein, denotes a group such as methoxy, ethoxy, n-propoxy, isoproxy, n-butoxy, t-butoxy, n-pentoxy, isopentoxy, neopentoxy, hexoxy and like groups attached to the remainder of the molecule by the oxygen atom.

The term "$(C_3–C_8)$cycloalkyl" includes cyclopropyl, cyclobutyl, cyclopentyl, cyclohexyl, cycloheptyl or cyclooctyl rings.

The term "protecting group" is used herein as it is frequently used in synthetic organic chemistry, to refer to a group which will prevent a functional group from participating in a reaction carried out on some other functional group of the molecule, but which can be removed when it is desired to do so. Such groups are discussed by T. W. Greene in chapters 5 and 7 of *Protective Groups in Organic Synthesis*, John Wiley and Sons, New York, 1981, and by J. W. Barton in chapter 2 of *Protective Groups in Organic Chemistry*, J. F. W. McOmie, e., Plenum Press, New York, 1973, which are incorporated herein by reference in their entirety.

Nitrogen protecting groups refer to a group which will prevent an amino group from participating in a reaction. Examples of amino protecting groups include benzyl and substituted benzyl such as 3,4-dimethoxybenzyl, o-nitrobenzyl, and triphenylmethyl; those of the formula —COOR$^1$ where R$^1$ includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. A preferred amino-protecting is phthalimidyl.

Useful compounds for practicing the method of the present invention includes pharmaceutically acceptable acid addition salts of the compounds defined by the above formula I. Acids commonly employed to form such salts are inorganic acids, such as hydrocholoric acid, hydrobromic acid, hydroiodic acid, sulfuric acid, phosphoric acid, and the like, and organic acids, such as p-toluenesulfonic, methane-sulfonic acid, oxalic acid, p-bromophenylsulfonic acid, carbonic acid, succinic acid, citric acid, benzoic acid, acetic acid, and the like.

Examples of such pharmaceutically acceptable salts thus are the sulfate, pyrosulfate, bisulfate, sulfite, bisulfite, phosphate, monohydrogenphosphate, dihydrogenphosphate, metaphosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and organic acids such as acetic acid, oxalic acid, maleic acid or fumaric acid Preferred Compounds of the Invention Preferred substituent groups of compounds of formula (I) include:

(a) R$^1$ is hydrogen or —$(C_1–C_6)$alkyl;

(b) R$^1$ is halo;

(c) R$^1$ is —$(C_1–C_6)$alkoxy;

(d) R$^2$ is hydrogen or —$(C_1–C_6)$alkyl;

(e) R$^2$ is halo;

(f) R$^2$ is Cl or F;

(g) R$^2$ is —$(C_1–C_6)$alkyl or —$(C_1–C_6)$alkoxy;

(h) R$^3$ is hydrogen;

(i) R$^3$ is —$(C_1–C_6)$alkyl;

(j) n is 1;

(k) m is 1;

(l) Z is —NH— or —CH$_2$—;

(m) Z is —N(COR)—;

(n) R is —$(C_1–C_6)$alkyl; and (o) R is —$(C_3–C_8)$cycloalkyl.

Compounds where R$^1$ is substituted at the 6-position and R$^2$ is substituted at the 2-position are preferred.

Of these particularly preferred compounds, compounds N-(2-(4-(2-methoxyphenyl)piperazin-1-yl)eth-1-yl)-3-(4-(6-fluoroindol-3-yl)-piperidin-1-yl)propanamide, N-(2-(4-(2-methoxyphenyl)piperazin-1-yl)eth-1-yl)-3-(4-(6-fluoroindol-3-yl)-1,2,3,6-tetrahydropyridin-1-yl) propanamide, N-(2-(4-(2-methoxyphenyl)piperazin-1-yl) eth-1-yl)-3-(4-(6-chloroindol-3-yl)-1,2,3,6- tetrahydropyridin-1-yl)propanamide, 1-(2-methoxyphenyl)-4-(6-(4-(6-chloroindole-3-yl)-1,2,3,6-tetrahydropyridin-1-yl)hex-1-yl)piperazine, N-(2-(4-(2-methoxyphenyl)piperazin-1-yl)eth-1-yl)-3-(4-(6-chloroindol-3-yl)-piperidin1-yl)propanamide, 1-(2-methoxyphenyl)-4-(6-(4-(6-fluoroindole-3-yl)-1piperidin-1-yl)hex-1-yl)piperazine trihydrochloride and 1-(2-methoxyphenyl)-4-(6-(4-(6-chloroindole-3-yl)-piperidin-1-yl)hex-1-yl)piperazine trihydrochloride are especially preferred.

Of these compounds, N-(2-(4-(2-methoxyphenyl)piperazin-1-yl)eth-1-yl)-3-(4-(6-fluoroindol-3-yl)-piperidin-1-yl)propanamide is most preferred.

Synthesis Methods

Compounds of the instant invention where Y is —CO— and Z is —NH— can be prepared as described in Scheme I, on the following page.

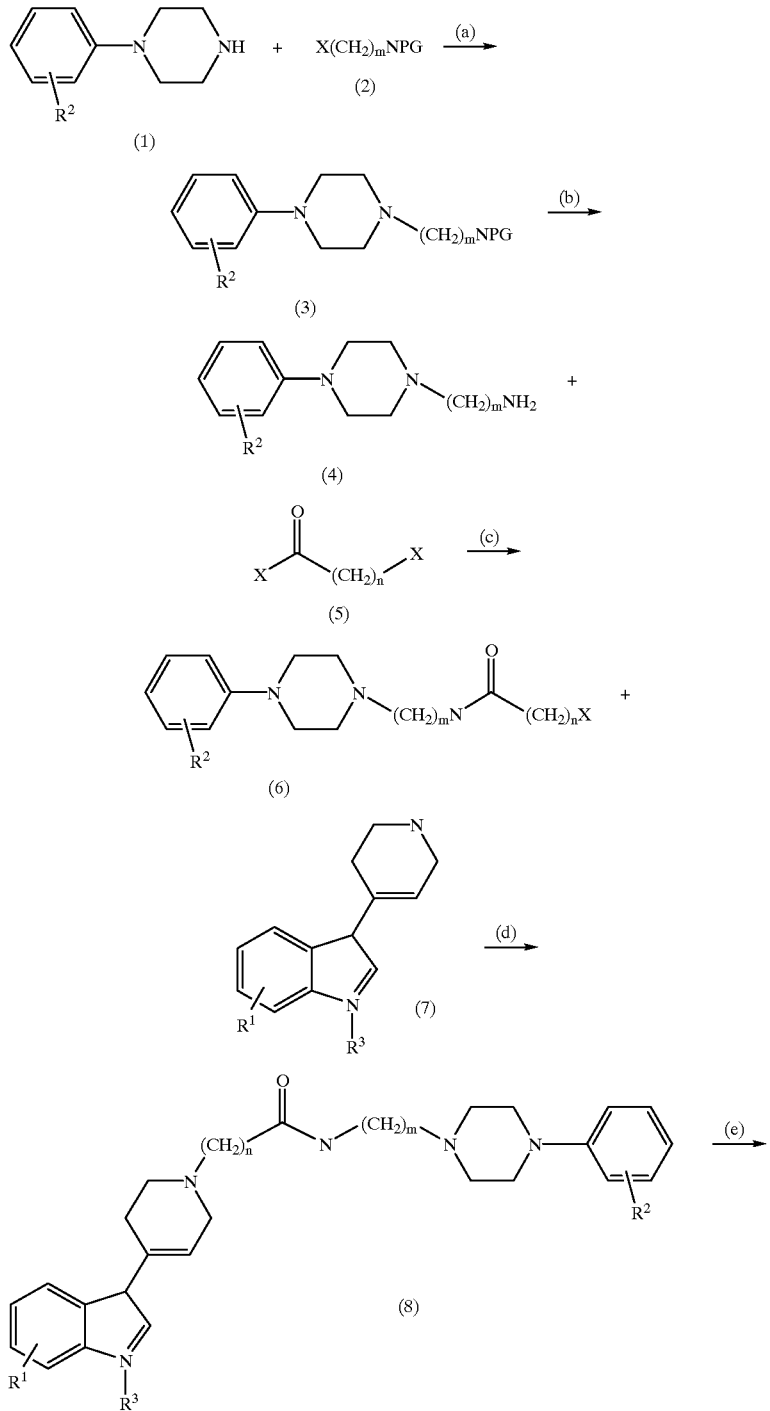

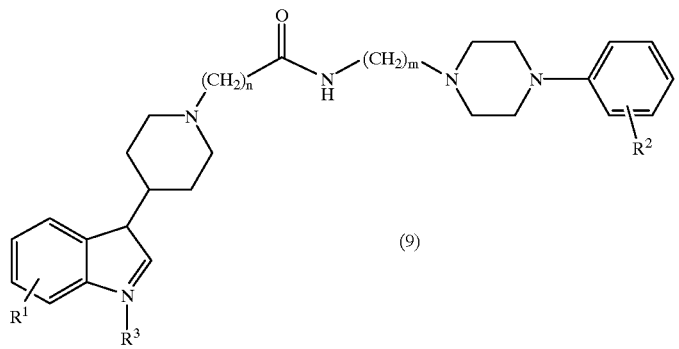

(9)

PG is a nitrogen protecting group
X is halo, preferably bromine or chlorine

An appropriately substituted piperazine (1) is N-alkylated with a protected haloalkylamine (2) by refluxing in a suitable solvent, such as acetonitrile, in the presence of an excess of a mild base, such as potassium carbonate, for about 1 to 10 hours to prepare (3). Phthalimidyl is a preferred protecting group.

Deprotection of (3) by, for example, treatment with hydrazine hydrate in ethanol, affords (4). N-acylation of the primary amine (4) can then be accomplished by treating a chilled solution of (4) with acyldihalide (5) in the presence of a base such as pyridine. Initial temperatures of about 0° C. are preferred for the reaction which is then allowed to warm to room temperature as it proceeds. Preferably, a halogenated hydrocarbon, such as methylene chloride, is employed as a solvent. The reaction is substantially complete in from 1 to 24 hours.

In a second alkylation step, (7) is coupled with (6) by refluxing together for from 1 to 24 hours in an appropriate solvent with a slight excess of a base such as triethylamine to prepare (8). Preferably, a co-solvent system, such as toluene/isopropanol is employed.

If desired, reduction of the tetrahydropyridine ring of (8) can be readily accomplished by treatment with a mild reducing agent such as triethyl silane in trifluoroacetic acid, preferably in an alkyl halide solvent such as methylene chloride.

Compounds where Y is —CH$_2$— and Z is —NH— or —N(COR)— can be prepared as described in Scheme II, below.

Scheme II

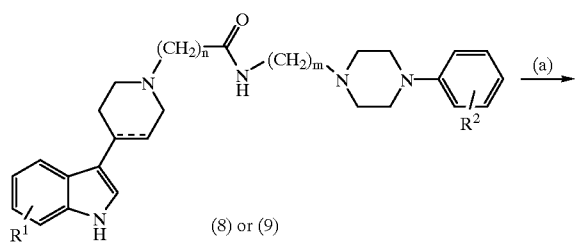

(8) or (9)

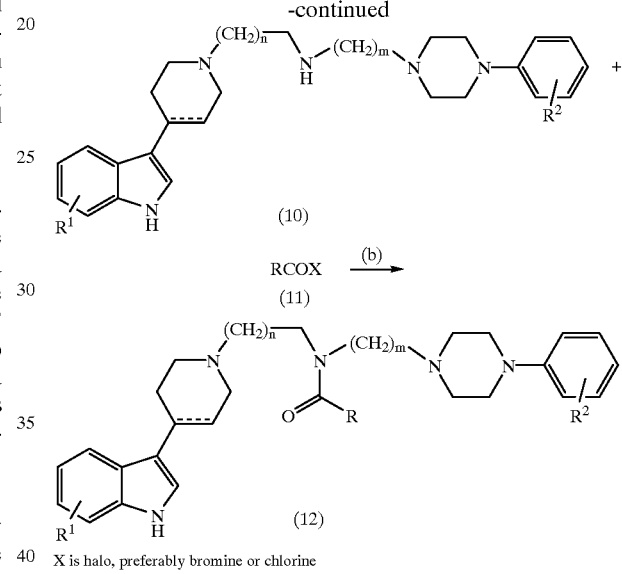

X is halo, preferably bromine or chlorine

Compounds where Y is —CH$_2$—, (10), are achieved by refluxing (8) or (9) with a suitable reducing agent, preferably lithium aluminum hydride, in an aprotic polar solvent such as tetrahydrofuran for from about 1 to 24 hours as shown in step (a), above.

Preparation of compounds where Z is —N(COR)— can be accomplished by acylation of (10) with an appropriate acylhalide (11) of the formula RCOX, where X is halo, preferably chlorine, as shown in step (b), above. Generally, a solution of (10) in an aprotic polar solvent such as tetrahydrofuran is treated with acylhalide (11), preferably dissolved and chilled to about 0° C. in tetrahydrofuran. The reaction is allowed to warm to room temperature and proceed until the reaction is complete in about 1 to 24 hours.

As described in Scheme 1, step (e), above, treatment with a reducing agent affords reduction of the tetrahydropyridine double bond.

When Y is —CO—, preparation of the desired compound may be accomplished by treating (8) or (9) with a base, such as sodium hydride then reacting with an acyl halide of the formula RCOX as described in part (b).

Compounds of formula I where Y and Z are each independently —CH$_2$— can be prepared as described in Scheme III, below.

Scheme III

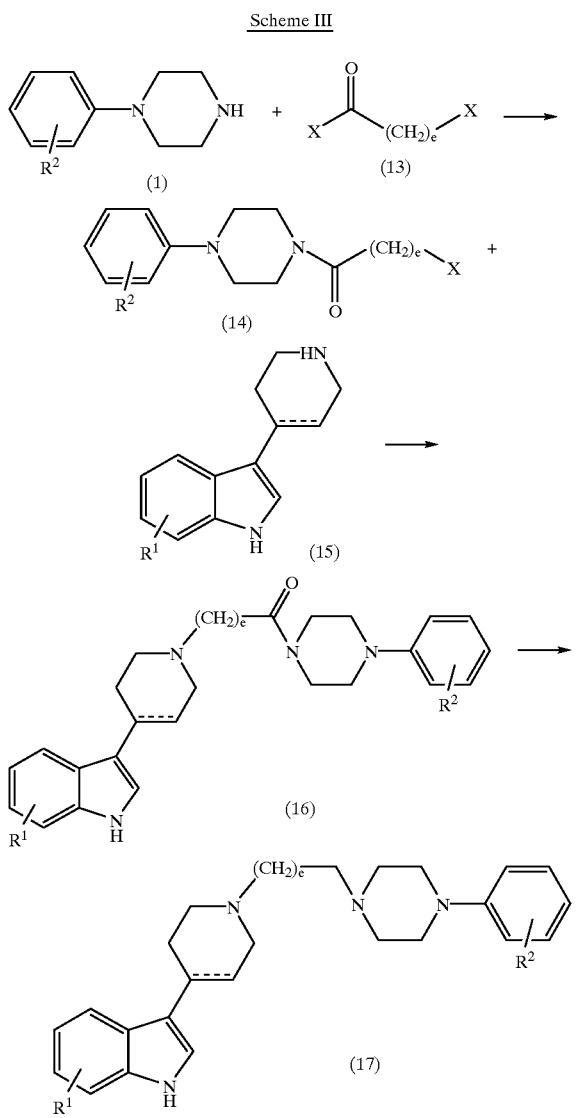

e is an integer from 3 to 7 both inclusive
X is halo, preferably bromine or chlorine.

Substituted piperazine (1) is acylated by treatment with acyldihalide (13). The reaction is preferably initiated at temperatures of about 0° C. in a suitable solvent, such as methylene chloride, in the presence of a slight excess of a base, such as pyridine, and allowed to warm to room temperature until substantially complete, in about 1 to 24 hours.

Alkylation of (14) is achieved as described in Scheme I, by refluxing (14) with (15) preferably in a co-solvent system of toluene/isopropanol, in the presence of an excess of a base such as triethylamine.

Reduction of the carbonyl of (16) can then be accomplished by refluxing with a reducing agent such as lithium aluminum hydride in an aprotic polar solvent such as tetrahydrofuran to prepare (17).

Further reduction of the tetrahydropyridine double bond can be accomplished as described in Scheme I, step (e), above.

The intermediates and final products may be isolated and purified by conventional techniques, for example, isolation using silica gel chromatography followed by recrystallization.

It will be readily appreciated by the skilled artisan that the starting materials which are not described are either commercially available or can be readily prepared by known techniques from commercially available starting materials. All other reactants used to prepare the compounds in the instant invention are commercially available.

The following preparations and examples further illustrate the preparation of the compounds of this invention. The examples are illustrative only and are not intended to limit the scope of the invention in any way.

EXAMPLE 1

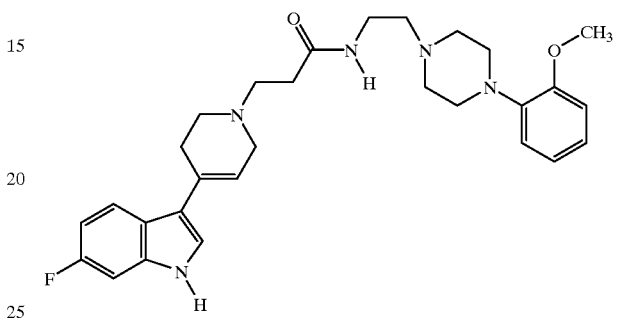

N-(2-(4-(2-methoxyphenyl)piperazin-1-yl)eth-1-yl)-
3-(4-(6-fluoroindol-3-yl)-1,2,3,6-tetrahydropyridin-
1-yl)propanamide A. 1-(2-methoxyphenyl)-4-[(2-phthalimido)ethyl]piperazine A solution of 1-(2-methoxyphenyl)piperazine (41.2 mmol) in 100 mL of acetonitrile and 12 mL of dimethylformamide was combined with N-(2-bromoethyl)phthalimide (43.3 mmol) and potassium carbonate (61.8 mmol). The mixture was heated to reflux for 8 hours. After cooling, the reaction mixture was quenched with water, extracted with dichloromethane. The organic phase was washed with brine, water, and dried over magnesium sulfate. Filtration and evaporation of the solvents gave a yellow oily residue that was purified by flash chromatography using hexanes and ethyl acetate (1:1) to give 1-(2-methoxyphenyl)-4-[(2-phthalimido)ethyl]piperazine (8.56 g, 57%).

B. 4-[(2-amino)ethyl]-1-(2-methoxyphenyl)piperazine

To a stirred solution of 1-(2-methoxyphenyl)-4-[(2-phthalimido)-ethyl] piperazine (23.4 mmol) in 160 mL of ethanol were added hydrazine hydrate (31 mL) and water (40 mL) The mixture was stirred at room temperature for 18 hours. The volatiles were evaporated. The residue was partitioned between ethyl acetate and saturated potassium carbonate solution. The organic layer was washed with brine and water, dried over magnesium sulfate, filtered and concentrated to give 4-[(2-amino)ethyl]-1-(2-methoxyphenyl)piperazine (5.45 g, 99%).

C. 4-[2-(3'-bromo)propionamido)ethyl]-1-(2-methoxyphenyl)piperazine

To a chilled solution (0° C.) of 4-[(2-amino)ethyl]-1-(2-methoxyphenyl)piperazine (10.46 mmol) in 40 mL of dichloromethane were added pyridine (12.55 mmol) and a solution of 3-bromopropionyl chloride (11.51 mmol) in 10 mL of dichloromethane. After addition, the reaction mixture was warmed to room temperature, and stirred for 1 hour. The reaction mixture was quenched with saturated sodium carbonate, extracted with dichloromethane. The organic phase was washed with brine, water, and dried over magnesium sulfate Filtration and evaporation of the solvents gave a residue that was purified by flash chromatography using 3–5% of methanol and 0.5% of ammonium hydroxide in ethyl acetate to give 4-[2-(3'-bromo)propionamido)ethyl]-1-(2-methoxyphenyl)piperazine (2.16 g, 56%).

D. N-(2-(4-(2-methoxyphenyl)piperazin-1-yl)eth-1-yl)-3-(4-(6-fluoroindol-3-yl)-1,2,3,6-tetrahydropyridin-1-yl)propanamide A mixture of 4-[2-(3'-bromo)propionamido)ethyl]-1-(2-methoxyphenyl)piperazine (1.63 mmol), 6-fluoro-3-(1,2,3,6-tetrahydropyridin-4-yl)-1H-indole (1.80 mmol) and triethylamine (1.96 mmol) was dissolved in 35 mL of toluene and 15 mL of isopropanol. The mixture was then heated to reflux for 14 hours. The volatiles were evaporated and the residue was purified by flash chromatography using 6% methanol, 0.5w ammonium hydroxide in ethyl acetate to give the title compound (588mg, 71%).

mp: 175–177° C.; ms: m/e 505 (M+); EA:

EXAMPLE 2

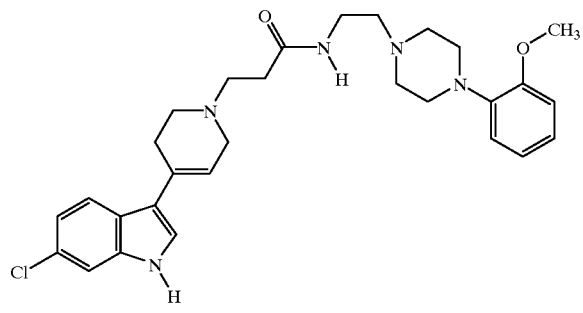

N-(2-(4-(2-methoxyphenyl)piperazin-1-yl)eth-1-yl)-3-(4-(6-chloroindol-3-yl)-1,2,3,6-tetrahydropyridin-1-yl)propanamide Following the procedures in Step 4 of EXAMPLE 1, the reaction of 4-[2-(3'-bromo)propionamido)ethyl]-1-(2-methoxyphenyl)piperazine (1.62 mmol) and 6-chloro-3-(1,2,3,6-tetrahydropyridin-4-yl)-1H-indole (1.79 mmol) gave the title compound (551 mg, 65%).

mp: 181–183° C.; ms: m/e=522 (M+);

EXAMPLE 3

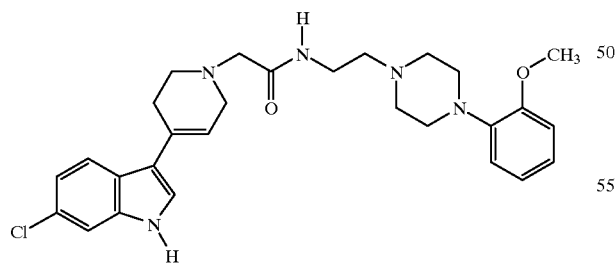

N-(2-(4-(2-methoxyphenyl)piperazin-1-yl)eth-1-yl)-2-(4-(6-chloroindol-3-yl)-1,2,3,6-tetrahydropyridin-1-yl)ethananamide A. 4-[2-(α-bromo)acetamido) ethyl]-1-(2-methoxyphenyl)piperazine Following the procedures in the Step 3 of EXAMPLE 1, the reaction of 4-[(2-amino) ethyl]-1-(2-methoxyphenyl)piperazine (4.19 mmol) and chloroacetyl chloride (4.68 mmol) gave 4-[2-(α-bromo)acetamido)ethyl]-1-(2-methoxyphenyl)piperazine (409 mg, 31%)

B. N-(2-(4-(2-methoxyphenyl)piperazin-1-yl)eth-1-yl)-2-(4-(6-chloroindol-3-yl) -1,2,3,6-tetrahydropyridin-1-yl) ethananamide Following the procedure in the Step 4 of EXAMPLE 1, the reaction of 4-[2-(a-bromo)acetamido)ethyl]-1-(2-methoxyphenyl)piperazine (1.31 4mol) and 6-chloro-3-(1,2,3,6-tetrahydropyridin-4-yl)-1H-indole (1.57 mmol) gave the title compound (339 mg, 51%).

mp: 89–93° C. (decompose). Elemental Analysis: Calculated: C, 66.08; H, 6.65; N, 13.54. Found: C, 66.19; H, 6.75; N, 13.78.

EXAMPLE 4

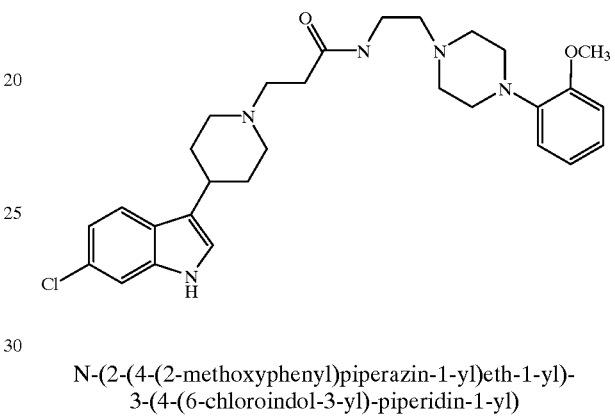

N-(2-(4-(2-methoxyphenyl)piperazin-1-yl)eth-1-yl)-3-(4-(6-chloroindol-3-yl)-piperidin-1-yl)propanamide A mixture of the compound of EXAMPLE 2 (0.383 mmol) and triethylsilane (0.422 mmol) in trifluoroacetic acid (6 ML) was stirred at 0° C. for 2.5 hours. The mixture was diluted with dichloromethane (20 mL) and quenched with sodium hydroxide solution until the pH was 10–13. The mixture was extracted with dichloromethane, dried over magnesium sulfate, filtered and concentrated. The residue was purified by flash chromatography using 8% methanol, 0.5% ammonium hydroxide in dichloromethane to give the title compound (191 mg, 95%).

mp: 69–71° C.; Elemental Analysis: Calculated: C, 66.46; H, 7.31; N, 13.36. Found: C, 66.67; H. 7.48; N, 13.43.

EXAMPLE 5

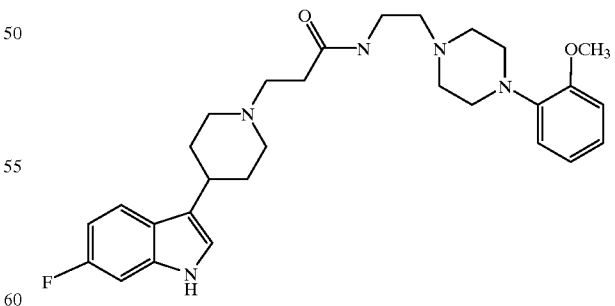

N-(2-(4-(2-methoxyphenyl)piperazin-1-yl)eth-1-yl)-3-(4-(6-fluoroindol-3-yl)-piperidin-1-yl)propanamide Following the same procedures reported in the EXAMPLE 4, the reduction of the compound of EXAMPLE 1 (0.396 mmol) gave the title compound (181 mg, 91%).

mp: 68–70° C.; Elemental Analysis: Calculated: C, 68.61; H, 7.55; N, 13.80. Found: C, 68.36; H, 7.63; N, 13.60.

EXAMPLE 6

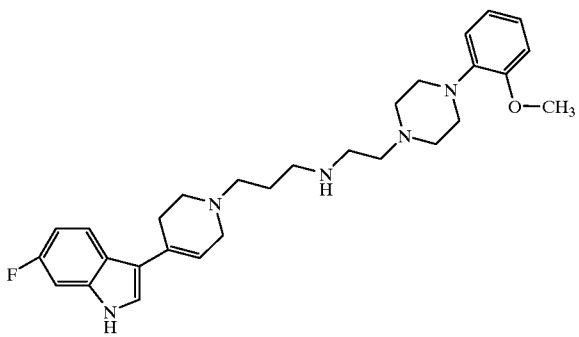

N-(2-(4-(2-methoxyphenyl)piperazin-1-yl)eth-1-yl)-N3-(4-(6-fluoroindol-3-yl)-1,2,3,6-tetrahydropyridin-1-yl)prop-1-ylamine To a stirred suspension of lithium aluminum hydride (6.72 mmol) in dry tetrahydrofuran (40 ml) was added dropwise a solution of the compound of EXAMPLE 1 (2.69 mmol) in tetrahydrofuran (30 mL) at room temperature. The mixture was heated to reflux until the starting material was consumed (18 hours). The excess of lithium aluminum hydride was carefully reacted with sodium sulfateolo water. After dilution with dichloromethane, the suspension was filtered. The filtrate was dried over magnesium sulfate, filtered, and then concentrated. The residue was purified by flash chromatography using 70 methanol, 1% ammonium hydroxide in dichloromethane to give the title compound (913 mg, 69%).

mp: 82–84° C.; ms: 492 (M$^+$); Elemental Analysis: Calculated: C, 70.85; H, 7.74; N, 14.24. Found: C, 70.66; H, 7.35; N, 13.86.

EXAMPLE 7

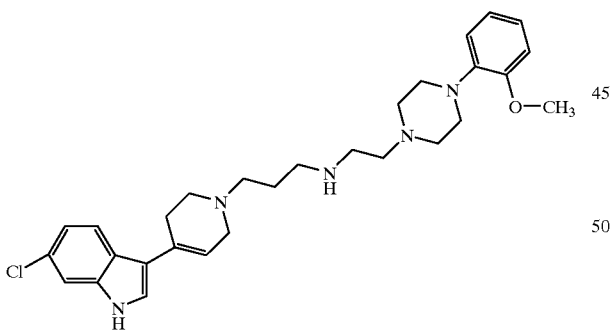

N-(2-(4-(2-methoxyphenyl)piperazin-1-yl)eth-1-yl)-N3-(4-(6-chloroindol-3-yl)-1,2,3,6-tetrahydropyridin-1-yl)prop-1-ylamine Following the same procedures reported in the EXAMPLE 6, the amide reduction of the compound of EXAMPLE 2 (1.29 mmol) with lithium aluminum hydride (3.23 mmol) in tetrahydrofuran gave the title compound (565 mg, 86%).

mp: 71–73° C.; ms: 508 (M$^+$); Elemental Analysis: Calculated: C, 68.55; H, 7.54; N, 13.78. Found: C, 68.15; H, 7.34; N, 13.53.

EXAMPLE 8

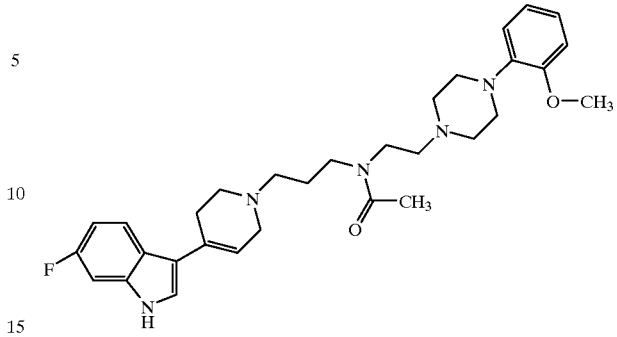

N-(2-(4-(2-methoxyphenyl)piperazin-1-yl)eth-1-yl)-N-3-(4-(6-fluoroindol-3-yl)-1,2,3,6-tetrahydropyridin-1-yl)prop-1-ylacetamide To a stirred solution of the compound of EXAMPLE 6 (1.02 mmol) and triethylamine (1.32 mmol) in 20 mL of dry tetrahydrofuran was added acetyl chloride (1.12 mmol) at 0° C. The reaction mixture was allowed to warm to room temperature and stirred for 2 hours. The mixture was quenched with saturated potassium carbonate solution and extracted with ethyl acetate. The organic phase was washed with brine and water, dried over magnesium sulfate, filtered and concentrated. The residue was purified by flash chromatography using 10–120 methanol, 1% ammonium hydroxide in dichloromethane to give the title compound (409 mg, 75%).

mp: 75–77° C.; Elemental Analysis: Calculated: C, 69.77; H, 7.55; N, 13.12. Found: C, 69.71; H, 7.36; N, 13.38.

EXAMPLE 9

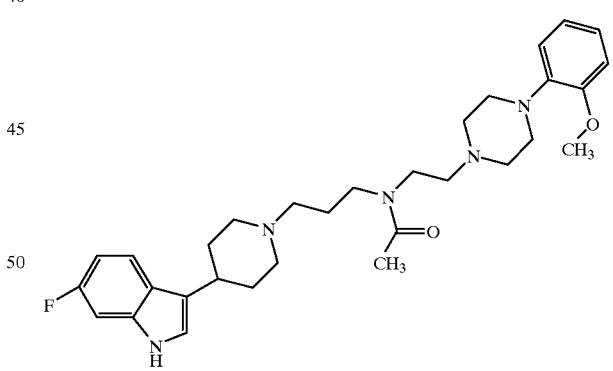

N-(2-(4-(2-methoxyphenyl)piperazin-1-yl)eth-1-yl)-N-3-(4-(6-fluoroindol-3-yl)-piperidine-1-yl)prop-1-ylacetamide trihydrochloride Following the same procedures reported in the EXAMPLE 4, the double bond reduction of the compound of EXAMPLE 8 (0.307 mmol) with triethylsilane (0.337 mmol) in trifluoroacetic acid followed by treatment with hydrochloric acid gave the title compound.

mp: 85–87° C.; ms: 645 (M$^+$);

EXAMPLE 10

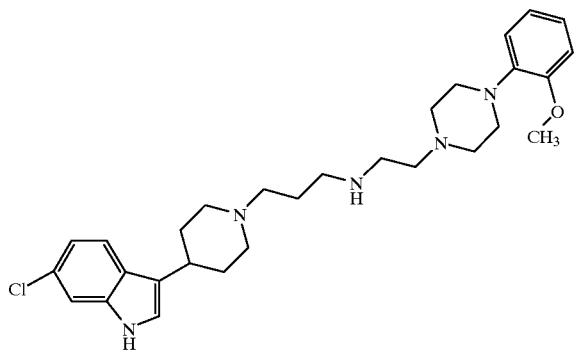

N-(2-(4-(2-methoxyphenyl)piperazin-1-yl)eth-1-yl)-N-3-(4-(6-chloroindol-3-yl)-piperidin-1-yl)prop-1-ylamine tetrahydrochloride Following the same procedures reported in the EXAMPLE 4, the double bond reduction of the compound of EXAMPLE 7 (0.520 mmol) with triethylsilane (0.572 mmol) in trifluoroacetic acid followed by treatment with hydrochloric acid gave the title compound (180 mg, 68%).

mp: 91–95° C.; ms (FD): m/e=511 (M$^+$); Elemental Analysis Calculated: C, 70.84; H, 7.79; N, 14.24. Found: C, 70.66; H, 7.35; N, 13.86.

EXAMPLE 11

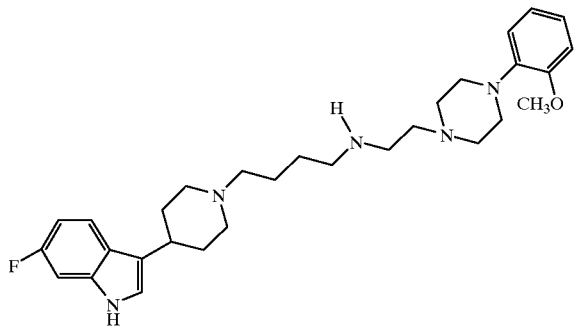

N-(2-(4-(2-methoxyphenyl)piperazine-1-yl)eth-1-yl)-N-3-(4-(6-fluoroindol-3-yl)-piperidin-1-yl)prop-1-ylamine tetrahydrochloride Following the same procedures reported in the EXAMPLE 4, the double bond reduction of the compound of EXAMPLE 6 (183 mg) with triethylsilane in trifluoroacetic acid followed by treatment with hydrochloric acid gave the title compound (154 mg, 84%).

mp: 172–174° C.; ms (FD): m/e=494 (M$^+$);

EXAMPLE 12

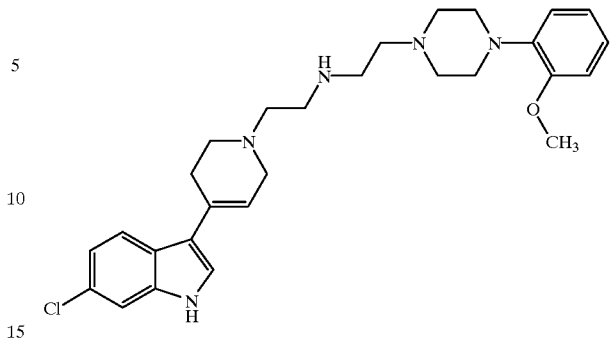

N-(2-(4-(2-methoxyphenyl)piperazin-1-yl)eth-1-yl), N-2-(4-(6-chloroindol-3-yl)-1,2,3,6-tetrahydropyridin-1-yl)eth-1-ylamine Following the same procedures reported in the EXAMPLE 6, the amide reduction of the compound of EXAMPLE 3 (0.340 mmol) with lithium aluminum hydride (1.02 mmol) in tetrahydrofuran gave the title compound (115 mg, 680).

mp: 78–80° C.; ms: (FD) m/e=494 )(M$^+$);

EXAMPLE 13

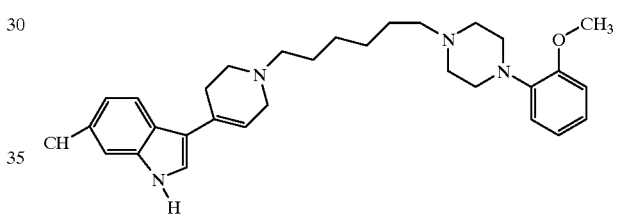

1-(2-methoxyphenyl)-4-(6-(4-(6-chloroindole-3-yl)-1,2,3,6-tetrahydropyridin-1-yl)hex-1-yl)piperazine A. 1-(2-methoxyphenyl)-4-(6-bromohexanoyl)piperazine To a stirred mixture of 1-(2-methoxyphenyl)piperazine (21.34 mmol) and pyridine (25.6 mmol) in 60 mL of dry dichloromethane was added dropwise a solution of 6-bromohexanoyl chloride (23.52 mmol) in 20 mL of dichloromethane at 0° C. under nitrogen. After addition, the mixture was allowed to warm to room temperature and stirred for 1–2 hours. The mixture was quenched with 10% potassium carbonate in water, and extracted with dichloromethane. The organic phase was washed with brine and water, dried over magnesium sulfate, filtered and concentrated. The residue was purified by flash chromatography using 5% methanol, 0.5% ammonium hydroxide in ethyl acetate to give 1-(2-methoxyphenyl)-4-(6-bromohexanoyl) piperazine (6.00 g, 76%).

B. 1-(2-methoxyphenyl)-4-(6-(4-(6-chloroindole)-3-yl)-1,2,3,6-tetrahydropyridin-1-yl)hexanoyl)piperazine A mixture of 1-(2-methoxyphenyl)-4-(6-bromohexanoyl) piperazine (1.79 mmol), 6-chloro-3-(1,2,3,6-tetrahydropyridin-4-yl)-1H-indole (1.97 mmol), and triethylamine (2.15 mmol) in 10 mL of toluene, 3 mL of isopropanol was heated to reflux for 14 hours. The volatiles were removed by evaporation, and the residue was purified by flash chromatography using 3% methanol, 0.5% ammonium hydroxide in ethyl acetate to give the alkylation product (557 mg, 60%).

C. 1-(2-methoxyphenyl)-4-(6-(4-(6-chloroindole-3-yl)-1,2,3,6-tetrahydropyridin-1-yl)hex-1-yl)piperazine Following the same procedures reported in the EXAMPLE 6, the amide reduction of the alkylated product from Step 2 (0.74 mmol) with lithium aluminum hydride (3.85 mmol) in tetrahydrofuran gave the title compound (253 mg, 67%).

mp: ms: EA: NMR:

EXAMPLE 14

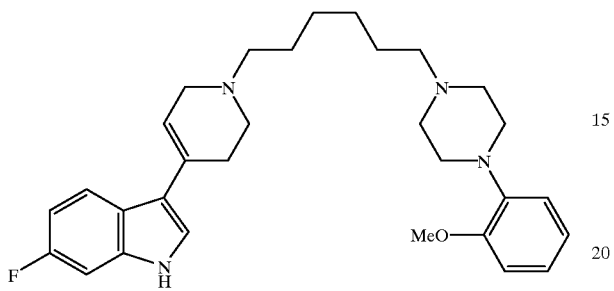

1-(2-methoxyphenyl)-4-(6-(4-(6-fluoroindole-3-yl)-1,2,3,6-tetrahydropyridin-1-yl)hex-1-yl)piperazine A. 1-(2-methoxyphenyl)-4-(6-(4-(6-fluoroindole-3-yl)-1,2,3,6-tetrahydropyridin-1-yl)hexanoyl)piperazine Following the same procedure reported in the Step 2 of EXAMPLE 13, the reaction of 1-(2-methoxyphenyl)-4-(6-bromohexanoyl)piperazine (2.37 mmol) with 6-fluoro-3-(1,2,3,6-tetrahydropyridin-4-yl)-1H-indole (2.37 mmol) and triethylamine (2.87 mmol) gave the alkylation product (780 mg, 65%).

B. 1-(2-methoxyphenyl)-4-(6-(4-(6-fluoroindole-3-yl)-1,2,3,6-tetrahydropyridin-1-yl)hex-1-yl)piperazine Following the same procedures reported in the EXAMPLE 6, the amide reduction of the alkylated product from Step 1 above (1.35 mmol) with lithium aluminum hydride (2.71 mmol) in tetrahydrofuran gave the title compound (653 mg, 996).

mp: 105–107° C.; ms(FD): m/e=490 (M+).

EXAMPLE 15

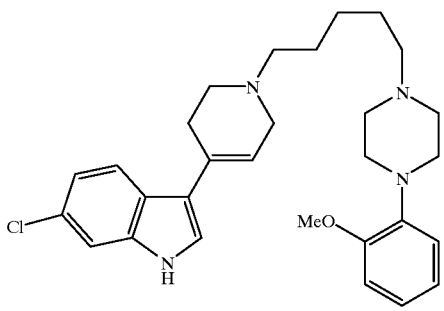

1-(2-methoxyphenyl)-4-(5-(4-(6-chloroindole-3-yl)-1,2,3,6-tetrahydropyridin-1-yl)pent-1-yl)piperazine A. 1-(2-methoxyphenyl)-4-(5-(4-(6-chloroindole-3-yl)-1,2,3,6-tetrahydropyridin-1-yl)valeryl)piperazine Following the same procedure reported in the Step 2 of EXAMPLE 13, the reaction of 1-(2-methoxyphenyl)-4-(5-bromovaleryl)piperazine (3.54 mmol) with 6-chloro-3-(1,2,3,6-tetrahydropyridin-4-yl)-1H-indole (3.54 mmol) and triethylamine (4.23 mmol) gave the alkylation product (715 mg, 40%).

B. 1-(2-methoxyphenyl)-4-(5-(4-(6-chloroindole-3-yl)-1,2,3,6-tetrahydropyridin-1-yl)pent-1-yl)piperazine Following the same procedures reported in the EXAMPLE 6, the amide reduction of the alkylated product from Step 1 above (1.26 mmol) with lithium aluminum hydride (2.52 mmol) in tetrahydrofuran gave the title compound (532 mg, 86%).

mp: 126–128° C. ms(FD): m/e=493 (M+).

EXAMPLE 16

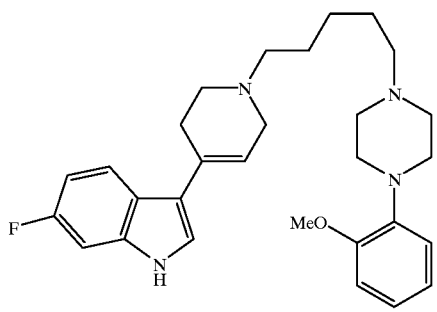

1-(2-methoxyphenyl)-4-(5-(4-(6-fluoroindole-3-yl)-1,2,3,6-tetrahydropyridin-1-yl)pent-1-yl)piperazine A. 1-(2-methoxyphenyl)-4-(5-(4-(6-fluoroindole-3-yl)-1,2,3,6-tetrahydropyridin-1-yl)valeryl)piperazine Following the same procedure reported in the Step 2 of EXAMPLE 13, the reaction of 1-(2-methoxyphenyl)-4-(5-bromovaleryl)piperazine (9.29 mmol) with 6-fluoro-3-(1,2,3,6-tetrahydropyridin-4-yl)-1H-indole (3.54 mmol) and triethylamine (4.63 mmol) gave the alkylation product (1.21 g, 53%). mp: 78–81° C.

B. 1-(2-methoxyphenyl)-4-(5-(4-(6-fluoroindole-3-yl)-1,2,3,6-tetrahydropyridin-1-yl)pent-1-yl)piperazine Following the same procedures reported in the EXAMPLE 6, the amide reduction of the alkylated product from Step 1 above (2.24 mmol) with lithium aluminum hydride (2.0 mmol) in tetrahydrofuran gave the title compound (908.2 mg, 85%).

mp: 69–71° C. ms(FD): m/e=476 (M+).

EXAMPLE 17

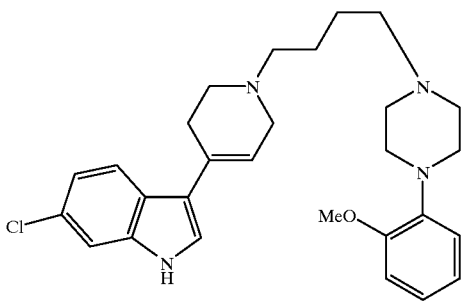

1-(2-methoxyphenyl)-4-(4-(4-(6-chloroindole-3-yl)-1,2,3,6-tetrahydropyridin-1-yl)but-1-yl)piperazine A. 1-(2-methoxyphenyl)-4-(4-(4-(6-chloroindole-3-yl)-1,2,3,6-tetrahydropyridin-1-yl)butyryl)piperazine Following the same procedure reported in the Step 2 of EXAMPLE 13, the reaction of 1-(2-methoxyphenyl)-4-(4-bromobuytryl)piperazine (3.04 mmol) with 6-chloro-3-(1,2,3,6-tetrahydropyridin-4-yl)-1H-indole (3.04 mmol) and triethylamine (3.66 mmol) gave the alkylation product (285 mg, 19%). mp: 93–95° C.

B. 1-(2-methoxyphenyl)-4-(4-(4-(6-chloroindole-3-yl)-1,2,3,6-tetrahydropyridin-1-yl)but-1-yl)piperazine Following the same procedures reported in the EXAMPLE 6, the amide reduction of the alkylated product from Step 1 above (0.517 mmol) with lithium aluminum hydride (1.03 mmol) in tetrahydrofuran gave the title compound (169.1 mg, 68%).

mp: 131–133° C.; ms(FD): m/e=479 (M$^+$).

EXAMPLE 18

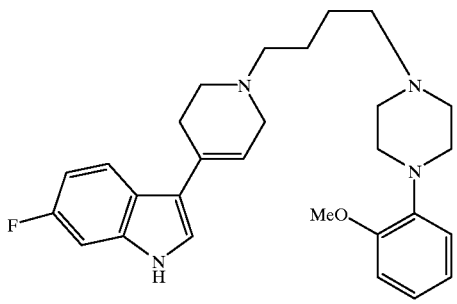

1-(2-methoxyphenyl)-4-(4-(4-(6-fluoroindole-3-yl)-1,2,3,6-tetrahydropyridin-1-yl)but-1-yl)piperazine A. 1-(2-methoxyphenyl)-4-(4-(4-(6-fluoroindole-3-yl)-1,2,3,6-tetrahydropyridin-1-yl)butyryl)piperazine Following the same procedure reported in the Step 2 of EXAMPLE 13, the reaction of 1-(2-methoxyphenyl)-4-(4-bromobuyryl)piperazine (3.43 mmol) with 6-fluoro-3-(1,2,3,6-tetrahydropyridin-4-yl)-1H-indole (3.43 mmol) and triethylamine (4.09 mmol) gave the alkylation product (284 mg, 18%). mp: 118–120° C.

B. 1-(2-methoxyphenyl)-4-(4-(4-(6-fluoroindole-3-yl)-1,2,3,6-tetrahydropyridin-1-yl)but-1-yl)piperazine Following the same procedures reported in the EXAMPLE 6, the amide reduction of the alkylated product from Step 1 above (0.516 mmol) with lithium aluminum hydride (1.03 mmol) in tetrahydrofuran gave the title compound (111.2 mg, 47%).

mp: 113–115° C.; ms (FD): m/e=473 (M$^+$+1).

EXAMPLE 19

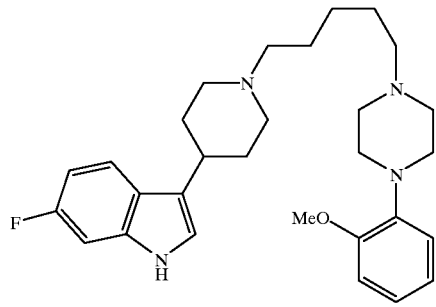

1-(2-methoxyphenyl) -4-(5-(4-(6-fluoroindole-3-yl)-piperidin-1-yl)pent-1-yl)piperazine trihydrochloride Following the same procedures reported in the EXAMPLE 4, the double bond reduction of the compound of EXAMPLE 16 (0.46 mmol) with triethylsilane (0.94 mmol) in trifluoroacetic acid gave the title compound (170 mg, 77%). The free base was converted to trihydrochloric salt with treatment with hydrochloric acid.

mp: 113–115° C.; ms(FD): m/e=480 (M$^+$+2).

EXAMPLE 20

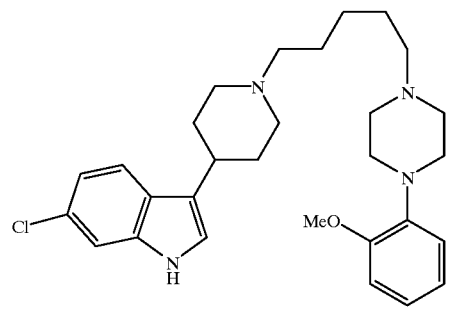

1-(2-methoxyphenyl) -4-(5-(4-(6-chloroindole-3-yl)-piperidin-1-yl)pent-1-yl)piperazine trihydrochloride Following the same procedures reported in the EXAMPLE 4, the double bond reduction of the compound of EXAMPLE 15 (0.42 mmol) with triethylsilane (0.94 mmol) in trifluoroacetic acid gave the title compound (170.8 mg, 82%). The free base was converted to trihydrochloric salt by treatment with hydrochloric acid.

mp: 139–141° C.; ms(FD): m/e=496 (M$^+$+1).

EXAMPLE 21

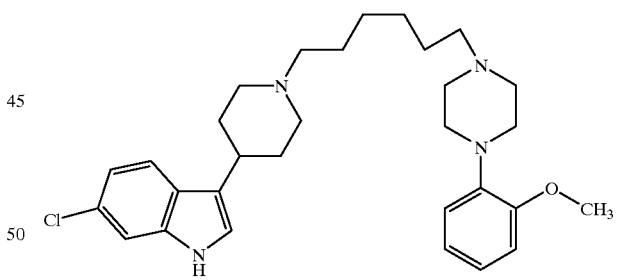

1-(2-methoxyphenyl)-4-(6-(4-(6-chloroindol-3-yl)-piperidin-1-yl)hex-1-yl)piperazine trihydrochloride Following the same procedures reported in the EXAMPLE 4, the double bond reduction of the compound of EXAMPLE 13 (0.50 mmol) with triethylsilane (0.63 mmol) in trifluoroacetic acid gave the title compound (201 mg, 79%). The free base was converted to trihydrochloric salt by treatment with hydrochloric acid.

mp: 185–187° C.; ms(FD): m/e=510 (M$^+$+1).

EXAMPLE 22

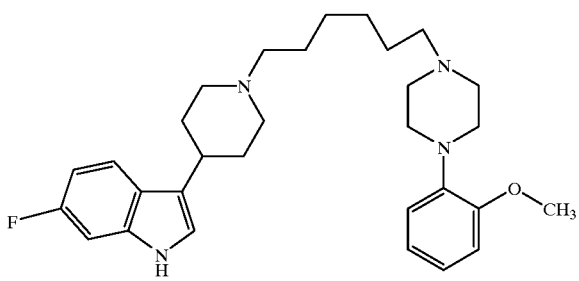

1-(2-methoxyphenyl)-4-(6-(4-(6-fluoroindol-3-yl)-piperidin-1-yl)hex-1-yl)piperazine trihydrochloride Following the same procedures reported in the EXAMPLE 4, the double bond reduction of the compound of EXAMPLE 14 (0.635 mmol) with triethylsilane (0.939 mmol) in trifluoroacetic acid gave the title compound (215.3 mg, 69%). The free base was converted to trihydrochloric salt by treatment with hydrochloric acid.

mp: 145–147° C.; ms(FD): m/e=494 (M$^+$+2).

The method of this invention is practiced by administering to a mammal a direct acting 5-HT$_{1D\alpha}$ antagonist and serotonin reuptake inhibitor or a pharmaceutically acceptable salt thereof. The phrase "direct acting 5-HT$_{1D\alpha}$ antagonist" as used in this specification and these claims means a non-endogenous chemical compound and includes: (1) synthetic chemical compounds (ligands) that block the action of serotonin on 5-HT$_{1D\alpha}$ receptors by directly inhibiting these receptors; and (2) partial agonists, which are synthetic chemical compounds (ligands) that block the action of serotonin on 5-HT$_{1D\alpha}$ receptors by directly inhibiting these receptors but produce a smaller maximal effect than do other ligands that act on the same receptor. These compounds may have activity at other receptors but must have some component of 5-HT$_{1D\alpha}$ antagonist activity.

Assay Experiments
Serotonin 1$_{D\alpha}$ receptor activity

The ability of the compounds of this invention to bind to the 5-HT$_{1D\alpha}$ receptor subtype was measured essentially as described in N. Adham, et al., *Proceedings of the National Academy of Sciences* (USA), 90, 408–412 (1993).

Membrane Preparation: Membranes were prepared from transfected LM(tk$^-$) cells which were grown to 100% confluency. The cells were washed twice with phosphate-buffered saline, scraped from the culture dishes into 5 ml of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 mL of buffer (50 mM Tris, 10 mM MgCl$_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio.). IC$_{50}$ values were converted to Ki values using the Cheng-Prusoff equation (*Biochem. Pharmacol.*, 22, 3099–3108 (1973). All experiments were performed in triplicate.

Representative compounds of the invention exhibited an Ki at the 5-HT$_{1A}$ and 5-HT$_{1D\alpha}$ receptors of at least 300 μmol.

As was reported by R. L. Weinshank, et al., WO93/14201, the 5-HT$_{1A}$ and 5-HT$_{1D}$ receptors are functionally coupled to a G-protein as measured by the ability of serotonin and serotonergic drugs to inhibit forskolin stimulated cAMP production in NIH3T3 cells transfected with the 5-HT$_{1A}$ or 5-HT$_{1D}$ receptors. Adenylate cyclase activity was determined using standard techniques. A maximal effect is achieved by serotonin. An Emax is determined by dividing the inhibition of a test compound by the maximal effect and determining a percent inhibition. (N. Adham, et al., supra,; R. L. Weinshank, et al., *Proceedings of the National Academy of Sciences* (USA), 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% CO$_2$. Drug dose-effect curves were then conducted by adding 6 different final concentrations of drug, followed immediately by the addition of forskolin (10 mM). Subsequently, the cells were incubated for an additional 10 minutes at 37 ° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioinmmunoassay (cAMP radioimmunoassay kit; Advanced Magnetics, Cambridge, Mass.). Radioactivity was quantified using a Packard COBRA Auto Gamma counter, equipped with data reduction software. Representative compounds were tested and found to be antagonists at the 5-HT$_{1A}$ and 5-HT$_{1D\alpha}$ receptor in the cAMP assay.

The efficacy of the compounds of Formula I to inhibit the reuptake of serotonin has been determined by a paroxetine binding essay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32M sucrose and 20 µM glucose. The preparations were resuspended after centrifugation by homogenizing in 50 volumes of cold reaction medium (50 µM sodium chloride, 50 µM potassium chloride, pH 7.4) and centrifuging at 50,000 g for 10 minutes. The process was repeated two times with a 10-minute incubation at 37° C. between the second and third washes. The resulting pellet was stored at −70° C. until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 µg protein/tube). Samples were incubated at 37° C. for 30 minutes; those containing 1 µM fluoxetine were used to determine nonspecific binding of $^3$H-paroxetine. After incubation, the tubes were filtered through Whatman GF/B filters, which were soaked in 0.05% polyethylenimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of Formulae XI and XIII by the above method showed potent reuptake activity, in many cases activity in the low nM range.

Pharmaceutical Formulations of the Invention

Throughout this document, the person or animal to be treated will be described as a "mammal", and it will be understood that the most preferred subject is a human. However it must be noted that the study of adverse conditions of the central nervous system in non-human animals is only now beginning, an that some instances of such treatments are coming into use. Accordingly, use of the present compounds in non-human animals is contemplated. It will be understood that the dosage ranges for other animals will necessarily be quite different from the doses administered to humans, and accordingly that the dosage ranges described be recalculated. For example, a small dog may be only $\frac{1}{10}^{th}$ of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin $1_{D\alpha}$ receptor provides a method of affecting the serotonin $1_{D\alpha}$ receptor which comprises administering to a subject in need of such treatment and effective amount of a compound of Formula I. Reasons for the necessity of affecting the $1_{D\alpha}$ receptor will be described in detail below, but in all cases the effect on the serotonin $1_{D\alpha}$ receptor is brought about through the compounds' potency as antagonists or partial agonists at that receptor. A mammal in need of a modification of the effects of the 5-HT$_{1D\alpha}$ receptors is one having one or more of the specific conditions and problems to be further described, or a condition or problem not yet recognized as created by an imbalance or malfunction of the 5-HT$_{1D}$ receptor, since research on the central nervous system is presently ongoing in many fields and newly discovered relationships between receptors and therapeutic needs are continually being discovered. In all cases, however, it is the compounds' ability to affect the serotonin $1_A$ or $1_{D\alpha}$ receptor which creates their physiological or therapeutic effects.

Further, the activity of compounds of Formula I in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula I will be set out in detail below. Again, the effective amount of a compound for the inhibition of serotonin reuptake, or for a specific therapeutic method which depends on the inhibition of reuptake, is determined in the manner described below.

The unique combination of 5-HT$_{1D\alpha}$ receptor activity and serotonin reuptake inhibition possessed by the compounds of Formula I afford a method of providing to a subject both physiological activities with a single administration of a compound of that formula. It is presently believed that the result of administration of a compound of Formula I is to provide physiological and therapeutic treatment methods which are typical of those provided by presently known serotonin reuptake inhibitors. In addition, of course, all of the physiological and therapeutic methods provided by compounds which affect the serotonin $1_{D\alpha}$ receptor are provided by the compounds of Formula I as well.

The activities of Formula I compounds at the 5-HT$_{1D\alpha}$ receptor and in reuptake inhibition are of comparable potencies, so a single effective amount is effective for both purposes.

The therapeutic and prophylactic treatments provided by this invention are practiced by administering to a mammal in need thereof a dose of a compound of formula I, or a pharmaceutically acceptable salt thereof, that is effective in inhibiting serotonin reuptake and the 5-HT$_{1D\alpha}$ receptor.

While it is possible to administer a compound employed in the methods of this invention directly without any formulation, the compounds are usually administered in the form of pharmaceutical formulation comprising a pharmaceutically acceptable excipient and at least one compound of the present invention. The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See, e.g., REMINGTON'S PHARMACEUTICAL SCIENCES, (16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets and injectable solutions. Especially preferred are capsules and tablets.

The therapeutic and prophylactic treatments provided by this invention are practiced by administering to a mammal in need thereof a dose of a compound of formula I or a pharmaceutically acceptable salt or solvate thereof that is effective to alleviate the pathological effects of $5-HT1_A$ and $5-HT_{1D\alpha}$ receptor-activated diseases.

The effective amount of compound to be administered, in general, is from about 1 to about 100 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day. It will be determined by a physician, in the light of all the relevant circumstances including the age, weight and response of the individual patient, the condition being treated and the severity of the patient's symptoms, the choice of compound to be administered and the choice of route of administration and therefore the above preferred dosage range is not intended to limit the scope of the present invention in any way.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

Therapeutic applications

The compounds of the invention are useful for treating a condition mediated by inhibiting the reuptake of serotonin such as anxiety, depression, obsessive-compulsive disease, obesity, migraine, pain, particularly neuropathic pain, bulimia, premenstrual syndrome or late luteal nasal dysphoric syndrome or PMDD (premenstral dysphonic disorder), alcoholism, tobacco abuse, panic disorder, anxiety, post-traumatic syndrome, memory loss, dementia of aging, social phobia, attention-deficit hyperactivity disorder, disruptive behavior disorders, impulsive control disorders, borderline personality disorder, chronic fatigue syndrome, premature ejaculation, erectile difficulty, anorexia nervosa, disorders of sleep, autism, mutism and trichotilomania, which comprises administering to a subject in need of such treatment a therapeutically effective amount of a compound of Formula I.

Pathological conditions mediated by inhibiting the $1_{D\alpha}$ receptor include depression, dementia, Parkinson's disease, anxiety, appetite modulation, sexual dysfunction, seasonal affective disorder, hyperprolactinemia, cerebral vascular disease, antisocial behavior, obsessive/compulsive disorder, amnesia, tardive dyskensia, hypertension and gastric motility disorder.

The following formulation examples may employ as active compounds any of the compounds of this invention. The examples are illustrative only and are not intended to limit the scope of the invention in any way.

Formulation 1

Hard gelatin capsules are prepared using the following ingredients:

|  | Quantity (mg/capsule) |
| --- | --- |
| N-(2-(4-(2-methoxyphenyl)piperazin-1-yl)eth-1-yl)-3-(4-(6-fluoroindol-3-yl)-1,2,3,6-tetrahydropyridin-1-yl)propanamide | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| N-(2-(4-(2-methoxyphenyl)piperazin-1-yl)eth-1-yl)-3-(4-(6-chloroindol-3-yl)-1,2,3,6-tetrahydropyridin-1-yl)propanamide | 250 |

-continued

| | Quantity (mg/tablet) |
|---|---|
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

| | Weight |
|---|---|
| N-(2-(4-(2-methoxyphenyl)piperazin-1-yl)eth-1-yl)-2-(4-(6-chloroindol-3-yl)-1,2,3,6-tetrahydropyridin-1-yl)ethananamide | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | Quantity (mg/tablet) |
|---|---|
| N-(2-(4-(2-methoxyphenyl)piperazin-1-yl)eth-1-yl)-2-(4-(6-chloroindol-3-yl)-1,2,3,6-tetrahydropyridin-1-yl)ethananamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | Quantity (mg/tablet) |
|---|---|
| N-(2-(4-(2-methoxyphenyl)piperazin-1-yl)eth-1-yl)-3-(4-(6-chloroindol-3-yl)-piperidin-1-yl)propanamide | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | Quantity (mg/tablet) |
|---|---|
| N-(2-(4-(2-methoxyphenyl)piperazin-1-yl)eth-1-yl)-N-3-(4-(6-fluoroindol-3-yl)-1,2,3,6-tetrahydropyridin-1-yl)prop-1-ylamine | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | Quantity (mg/tablet) |
|---|---|
| N-(2-(4-(2-methoxyphenyl)piperazin-1-yl)eth-1-yl)-N-3-(4-(6-chloroindol-3-yl)-1,2,3,6-tetrahydropyridin-1-yl)prop-1-ylamine | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

We claim:

1. A compound of the formula (I)

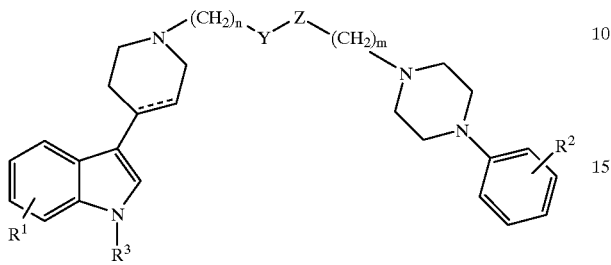

Wherein
$R_1$ and $R_2$ are each independently hydrogen, halo, —($C_1$–$C_6$)alkyl or —($C_1$–$C_6$)alkoxy;
$R^3$ is hydrogen or —($C_1$–$C_6$)alkyl;
Y is —CO— or —$CH_2$—;
Z is —NH—, —N(COR)— or $CH_2$— where R is —($C_1$–$C_6$)alkyl or —($C_3$–$C_8$)cycloalkyl;
═represents a double or single bond;
n and m are an each independently integer from 1 to 3, both inclusive; or a pharmaceutically acceptable salt thereof.

2. A compound as claimed in claim 1 wherein $R_1$ is substituted at the 6-position and $R^2$ is substituted at the 2-position.

3. A compound as claimed in claim 2 wherein $R_1$ is halo and $R^2$ is ($C_1$–$C^6$)alkoxy.

4. A compound as claimed in claim 2 selected from the group consisting of:
  N-(2-(4-(2-methoxyphenyl)piperazin-1-yl)eth-1-yl)-3-(4-(6-fluoroindol-3-yl)-piperidin-1-yl)propanamide,
  N-(2-(4-(2-methoxyphenyl)piperazin-1-yl)eth-1-yl)-3-(4-(6-fluoroindol-3-yl-1,2,3,6-tetrahydropyridin-1-yl) propanamide,
  N-(2-(4-(2-methoxphenyl)piperazin-1-yl)eth-1-yl)-3-(4-(6-chloroindol-3-yl)-1,2,3,6-tetrahydropyridin-1-yl) propanamide,
  1-(2-methoxyphenyl)-4-(6-(4-(6-chloroindole-3-yl)-1,2,3,6-tetrahydropyridin-1-yl)hex-1-yl)piperazine,
  N-(2-(4-(2-methoxyphenyl)piperazin-1-yl)eth-1-yl)-3-(4-(6-chloroindol-3-yl)-piperidin 1-yl)propanamide,
  1-(2-methoxyphenyl)-4-(6-(4(6-fluoroindole-3-yl)-piperidin-1-yl)hex-1-yl)piperazine and 1-(2-methoxypheny)-4-(6-(4-(6-chloroindole-3-yl)-piperidin-1-yl)hex-1-yl)piperazine or a pharmaceutically accepted salt thereof.

5. The Compound of claim 4 which is N-(2(4(2-methoxyphenyl)piperazin-1-yl)eth 1-yl)-3-(4(6-floroundol-3-yl)-piperidin-1-yl)propanamide or a pharmaceutically acceptable carrier or diluent thereof.

6. A compound according to claim 4 selected from the group consisting of 1-(2-methoxphenyl)-4-(6-(4-(6-fluoroindole-3-yl)-piperidin-1-yl)hex-1-yl)piperazine trihydrochloride and 1-(2-methoxyphenyl)-4-(6-(4-(6-chloroindole-3-yl)-piperidin-1-yl)hex-1-yl)piperazine trihydrochloride.

7. A pharmaceutical formulation comprising a compound of formula I as claimed in claim 1 with pharmaceutically acceptable carriers or diluent thereof.

8. A method of alleviating the pathological effects of depression in a mammal by administering to the mammal a pharmaceutically effective amount of a compound of formula I as claimed in claim 1.

9. The method of claim 8 wherein the mammal is a human.

* * * * *